United States Patent [19]

Ellsworth

[11] Patent Number: 4,548,604

[45] Date of Patent: Oct. 22, 1985

[54] ADJUSTABLE DIAPER

[76] Inventor: Laurett Ellsworth, 370 E. 400 South, Provo, Utah 84601

[21] Appl. No.: 437,039

[22] Filed: Oct. 27, 1982

[51] Int. Cl.³ .............................................. A61F 13/16
[52] U.S. Cl. ................................. 604/399; 604/385 A
[58] Field of Search ......... 604/399, 386, 387, 400–402, 604/385

[56] References Cited

U.S. PATENT DOCUMENTS

| 2,604,097 | 7/1952 | White | 604/399 |
| 2,606,558 | 8/1952 | Kennette | 604/399 |
| 2,703,577 | 3/1955 | May | 604/399 |
| 2,815,026 | 12/1957 | Meyer | 604/399 |
| 2,868,205 | 1/1959 | Epstein | 604/399 |
| 3,050,063 | 8/1962 | Margraf | 604/399 |
| 3,162,196 | 12/1964 | Salk | 604/399 |
| 3,176,688 | 4/1965 | Tschappat | 604/399 |
| 3,530,859 | 9/1970 | Heimowitz | 604/399 |
| 4,324,245 | 4/1982 | Mesek et al. | 604/385 |

Primary Examiner—C. Fred Rosenbaum
Assistant Examiner—Sherri Vinyard
Attorney, Agent, or Firm—B. Deon Criddle

[57] ABSTRACT

A cloth diaper garment fabricated of a double layer of cloth and having an elastic member attached to the outer edge of the diaper through most of the perimeter of the garment. The diaper employs metal snaps arranged to permit use of the diaper with different sized infants.

2 Claims, 4 Drawing Figures

ADJUSTABLE DIAPER

BACKGROUND OF THE INVENTION

1. Field of the Invention

The present invention pertains to garments and in particular, to adjustable cloth diapers.

2. Prior Art

Cloth diapers with snap fasteners have long been known. See, for example, U.S. Pat. Nos. 2,347,867 (Alban); 2,620,798 (O'Brien); 2,621,656 (Dotson); 2,607,348 (Rosenblatt); 2,969,065 (Farnsworth); 2,718,888 (Meroney); 3,417,751 (Murdock); 3,530,859 (Heimowitz); 3,431,908 (Lee); 3,359,980 (Rosenblatt); 3,176,688 (Tschappat).

Many prior art diapers disclose various unique fastening means in an attempt to avoid the use of pins and other sharp objects which constitute a hazard to a young child or that may become separated and lost from the diaper. Others of the prior art diapers are designed to contain padding or other absorbent materials. Still other prior art diapers utilize structural features such as elastic bands, to provide a better fit than is otherwise attainable with older, rectangularly shaped fabric.

A common fastening means employed with adjustable cloth diapers consists of a series of metal snaps arranged to permit variable overlapping of diaper portions to achieve distinct sizes. However, merely changing the waist size of a diaper is not entirely satisfactory since the infant body length also changes during growth. Consequently, the consumer is faced with the need to purchase different sizes of diapers as a baby grows in size in order to continually achieve an acceptible fit. Also, diapers should fit snugly, but without restrictive binding around the legs of the infant and should allow for free leg movement.

Additional considerations in the construction of a diaper are the need to minimize threads and seams in order to prevent chafing of the baby's body and to prevent leakage. Also, diapers should have the capability for the use of inserts for nighttime use. In addition, the diapers should be designed in such a way that they may be quickly and easily put on or taken off. Finally, the fabric construction of the diaper should be such that liquid wastes are drawn away from the baby's body to reduce chafing and insure comfort.

OBJECTS OF THE INVENTION

A principal object of the present invention is to provide an adjustable diaper garment.

Another object of the present invention is to provide an adjustable diaper garment that is adaptable over a very wide size range while using a minimum number of snap fasteners.

Still another object of the present invention is to provide an adjustable diaper garment that is adaptable for use with an inside liner for nighttime use or when it is not practical to change the infant's diaper for extended time periods.

Yet another object of the present invention is to provide an adjustable diaper garment that has a high capacity for absorbing liquid wastes.

PRINCIPAL FEATURES OF THE INVENTION

Principal features of the invention include a main diaper body comprised of two layers of cotton fabric sewn around its edges. The main body is of a generally hourglass shape. A panel of fabric batting is sewn into the center of the main body, i.e. the section comprising the crotch section of the main body. Elastic strips are inserted into the leg portions of the diaper and continue along the edges towards a rear upper panel where another elastic band extends along an upper edge to cause the corners to gather and fold inwardly around a baby's body.

An inside liner, also having a generally hourglass configuration is arranged to snap to the interior of the main body when additional absorbency is required.

Other objects and features of the invention will become apparent from the following detailed description and drawing disclosing what is presently contemplated as being the best mode of the invention.

THE DRAWING

In the drawing:

FIG. 1 is a top plan view of the main body of the diaper invention;

FIG. 2, a cross-sectional view taken on the line 2—2 of FIG. 1;

FIG. 3, a top plan view of the inside liner; and

FIG. 4, a cross-section view taken on the line 4—4 of FIG. 3.

DETAILED DESCRIPTION OF THE INVENTION

Figure 1:
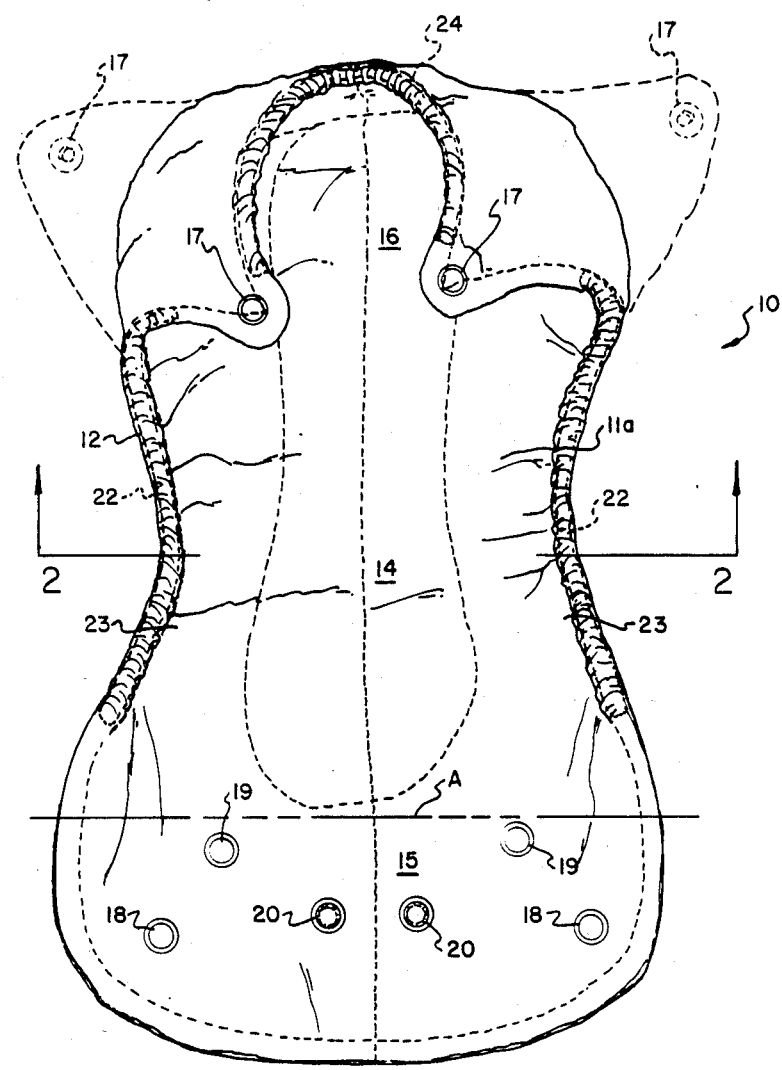

Referring now to the drawings:

In the illustrated preferred embodiment, the main body of the diaper garment, shown generally at 10, is formed from two hourglass shaped pieces of fabric 11a and 11b, sewn together along the perimeter 12 of the diaper 10.

Figure 2:
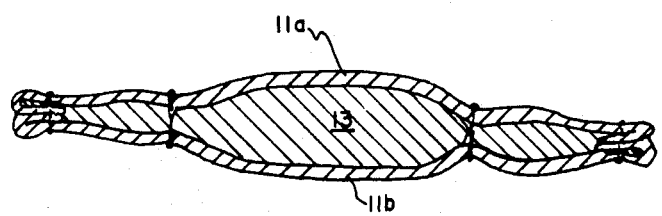

A fabric batting 13 is sewn between the two layers of fabric 11a and 11b, as shown in FIG. 2, and is folded in such a manner as to be thicker in the area of a crotch panel 14.

The diaper, as formed, is divided generally into three zones forming the crotch panel 14, a front flap panel 15 and rear flap panel 16.

The diaper 10 is fastened for use by a plurality of conventional snap assemblies. Front male snaps 17 at opposite upper corners of the diaper are fastened to either a first pair of outer and upper female snaps 18 or a second pair of inner and lower female snaps 19 at one side of the diaper in accordance with the size of the infant and the size diaper desired when front flap panel 15 is folded upwardly towards the baby's stomach. The same diaper can be used for very small babies by folding flap 15 down along the line A and then securing snaps 17 to a third pair of inner female snaps 20 at an opposite side of the diaper. This not only provides a small waist line, but also provides for a shortened body length of the diaper.

The perimeter of diaper body 11 has elastic strips 22 sewn to the fabrc layer sides adjacent to the crotch section 14 and forming leg portions 23 and an elastic band 24 across the top edge of rear section 16. The interaction of the elastic bands in the leg portions 21 and the band on the upper edge of rear section 16 gather the fabric to give the rear section 16 a generally concave shape in the area of snaps 17, with the corners containing the snaps then being turned in and slightly down.

When an infant is very small, the pre-formed diaper of the invention is too large in both waist size and body length if used merely by folding the front flap up between the infant's legs and connecting snaps. By folding the diaper along line A and then folding the front flap between the baby's legs to engage snaps 17 and snaps 20, the diaper length is effectively shortened. At the same time, the waist is made smaller and the leg portions can effectively close around the upper legs of the infant.

For larger babies, the front flap is merely folded up between the infant's legs and the snaps 17 are attached to either the snaps 18 or the snaps 19 to give the desired diaper fit.

With larger babies, particularly, it is presently common to use a double diaper or extra absorbent pads for a "night diaper" or at other times when it may be inconvenient to change the baby's diaper for extended time periods. When such extra pads are used, the pads sometimes bunch up to make the infant uncomfortable and because of their bulk, they do not always fit closely around the infant's legs.

Figure 3:
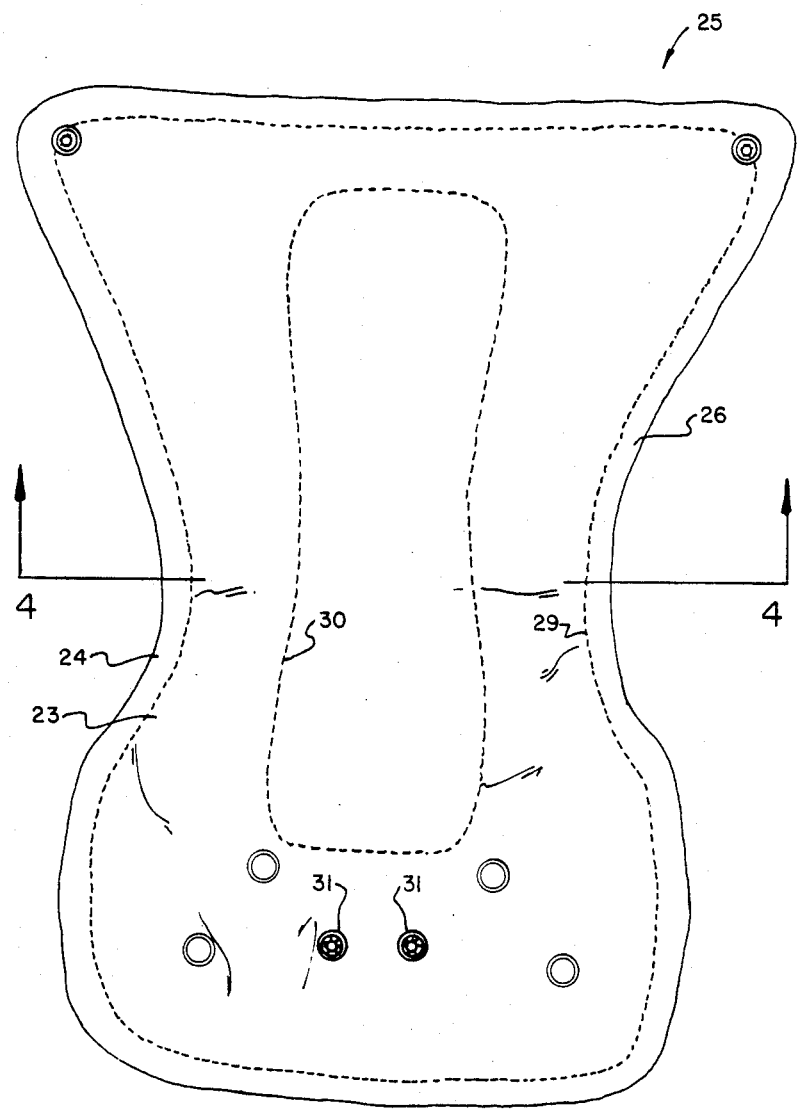
Figure 4:
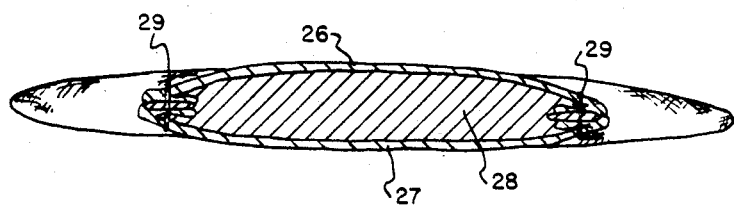

With the present invention, an inside liner 25 (FIG. 3) is made from two hour-glass pieces of fabris 26 and 27 shaped to fit inside the periphery of the main body 10, with absorbent batting 28 therebetween. The outer edges of the fabric pieces are sewn together by a seam 29 and by another seam 30 in the central area of the liner that also holds the batting in place. A pair of male snaps 31 are at the central top of the liner to snap into the female snaps 20.

It will be apparent that the male and female snaps disclosed herein can be reversed or that other types of snap fasteners can be used.

Although a preferred embodiment of my invention is herein described, it is to be understood that the present disclosure is by way of example and that variations are possible without departing from the subject matter coming within the scope of the following claims, which subject matter I regard as my invention.

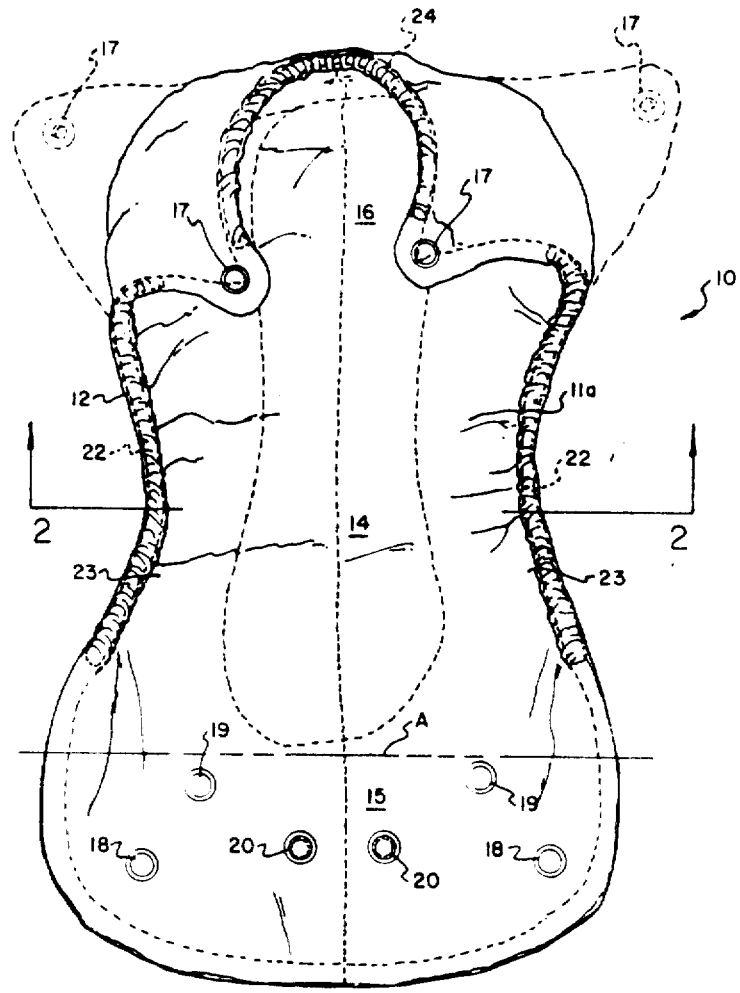

I claim:

1. A diaper garment for infants comprising:

an absorbent main body, having inner and outer faces with reference to an infant wearing said diaper, and providing a front flap panel, a rear flap panel, and a crotch panel comprised of a plurality of fabric layers attached to a top edge, bottom edge and side edges forming a perimeter of said layers;

a layer of fabric batting containing within the fabric layers of said main body, said batting being folded to provide a thickened center crotch panel;

elastic members sewn into the side edges and top edge of said main body, whereby the corners at the junctions of the side and the top edges are turned inwardly;

a male snap at the inner face of each corner at the junctions of the side and top edges;

a first pair of female snaps at the outer face with each snap of said pair being each proximate a corner formed by the junctions of the side and bottom edges;

a second pair of spaced apart female snaps at the outer face and spaced inwardly and towards the crotch panel from the female snaps proximate the corners formed by the bottom and side edges; and a third pair of spaced apart female snaps at the inner face proximate the top edge, the second pair of the female snaps being spaced closer together than the snaps of the first pair of female snaps and the third pair of female snaps being spaced closer together than the snaps of the second pair of female snaps.

2. A diaper as in claim 1, further including an insert liner comprising a pair of pieces of fabric having an hour-glass configuration and fitting within the periphery of the absorbent main body, said fabric pieces being sewn together with absorbent batting material therebetween and having a pair of male snaps at one top edge thereof to connect to the third pair of female snaps at the inner face of the absorbent main body.

* * * * *

UNITED STATES PATENT AND TRADEMARK OFFICE
CERTIFICATE OF CORRECTION

PATENT NO. : 4,548,604

DATED : October 22, 1985

INVENTOR(S) : Laurett Ellsworth

It is certified that error appears in the above-identified patent and that said Letters Patent is hereby corrected as shown below:

The title page showing the illustrative figure should be deleted to appear as per attached title page.

Signed and Sealed this

Second Day of September 1986

[SEAL]

Attest:

DONALD J. QUIGG

Attesting Officer

Commissioner of Patents and Trademarks

United States Patent [19]

Ellsworth

[11] Patent Number: 4,548,604
[45] Date of Patent: Oct. 22, 1985

[54] ADJUSTABLE DIAPER

[76] Inventor: Laurett Ellsworth, 370 E. 400 South, Provo, Utah 84601

[21] Appl. No.: 437,039

[22] Filed: Oct. 27, 1982

[51] Int. Cl.⁴ ............................................. A61F 13/16
[52] U.S. Cl. ............................. 604/399; 604/385 A
[58] Field of Search ........ 604/399, 386, 387, 400–402, 604/385

[56] References Cited

U.S. PATENT DOCUMENTS

| | | | |
|---|---|---|---|
| 2,604,097 | 7/1952 | White | 604/399 |
| 2,606,558 | 8/1952 | Kennette | 604/399 |
| 2,703,577 | 3/1955 | May | 604/399 |
| 2,815,026 | 12/1957 | Meyer | 604/399 |
| 2,868,205 | 1/1959 | Epstein | 604/399 |
| 3,050,063 | 8/1962 | Margraf | 604/399 |
| 3,162,196 | 12/1964 | Salk | 604/399 |
| 3,176,688 | 4/1965 | Tschappat | 604/399 |
| 3,530,859 | 9/1970 | Heimowitz | 604/399 |
| 4,324,245 | 4/1982 | Mesek et al | 604/385 |

Primary Examiner—C. Fred Rosenbaum
Assistant Examiner—Sherri Vinyard
Attorney, Agent, or Firm—B. Deon Criddle

[57] ABSTRACT

A cloth diaper garment fabricated of a double layer of cloth and having an elastic member attached to the outer edge of the diaper through most of the perimeter of the garment. The diaper employs metal snaps arranged to permit use of the diaper with different sized infants.

2 Claims, 4 Drawing Figures